United States Patent
Borges et al.

(10) Patent No.: US 8,088,156 B2
(45) Date of Patent: Jan. 3, 2012

(54) GRAFT MATERIAL ATTACHMENT DEVICE AND METHOD

(75) Inventors: Juan Borges, Miami Lakes, FL (US);
Clifford J. Dwyer, Weston, FL (US);
William L. Howat, Weston, FL (US)

(73) Assignee: Cordis Corporation, Bridgewater, NJ (US)

( * ) Notice: Subject to any disclaimer, the term of this patent is extended or adjusted under 35 U.S.C. 154(b) by 107 days.

(21) Appl. No.: 10/680,805

(22) Filed: Oct. 7, 2003

(65) Prior Publication Data

US 2005/0075715 A1 Apr. 7, 2005

(51) Int. Cl.
*A61F 2/06* (2006.01)
(52) U.S. Cl. .................. 623/1.13; 623/1.44; 606/151
(58) Field of Classification Search ............... 623/1.11, 623/1.13, 1.36; 606/151
See application file for complete search history.

(56) References Cited

U.S. PATENT DOCUMENTS

| | | | | |
|---|---|---|---|---|
| 5,476,507 A * | 12/1995 | Wakabayashi et al. | ...... | 623/1.54 |
| 5,527,355 A * | 6/1996 | Ahn | ............... | 623/1.36 |
| 5,711,960 A * | 1/1998 | Shikinami | ............. | 424/426 |
| 6,132,457 A * | 10/2000 | Chobotov | ............. | 623/1.13 |
| 6,273,917 B1 * | 8/2001 | Inoue | ................. | 623/23.64 |
| 6,342,059 B1 | 1/2002 | Chevillon et al. | | |
| 6,482,227 B1 * | 11/2002 | Solovay | ............. | 623/1.13 |
| 6,511,506 B2 * | 1/2003 | Chevillon et al. | ..... | 623/1.36 |
| 6,699,277 B1 | 3/2004 | Freidberg et al. | | |
| 6,805,706 B2 * | 10/2004 | Solovay et al. | ........ | 623/1.15 |
| 2002/0002397 A1 | 1/2002 | Martin et al. | | |
| 2002/0165603 A1 * | 11/2002 | Thornton et al. | ....... | 623/1.13 |
| 2003/0088305 A1 * | 5/2003 | Van Schie et al. | ...... | 623/1.12 |

FOREIGN PATENT DOCUMENTS

| | | |
|---|---|---|
| JP | 53-131357 | 4/1977 |
| WO | WO 00/54822 A2 | 9/2000 |

OTHER PUBLICATIONS

European Search Report for EP 04 25 6158 dated Apr. 14, 2005.

* cited by examiner

*Primary Examiner* — Thomas J Sweet
*Assistant Examiner* — Christopher D Prone
(74) *Attorney, Agent, or Firm* — Carl J. Evens

(57) ABSTRACT

A stent-graft fabricated from a thin-walled, high strength material provides for a more durable and lower profile endoprosthesis. The stent-graft comprises one or more stent segments covered with a fabric formed by the weaving, knitting or braiding of a biocompatible, high tensile strength, abrasion resistant, highly durable yarn such as ultra high molecular weight polyethylene. The one or more stent segments may be balloon expandable or self-expanding. The fabric may be attached to the stent segments utilizing any number of known materials and techniques. The fabric may be attached to the stent segments utilizing an attachment device that secures the fabric to a strut of the stent segment by sandwiching the fabric between itself and the stent strut.

11 Claims, 8 Drawing Sheets

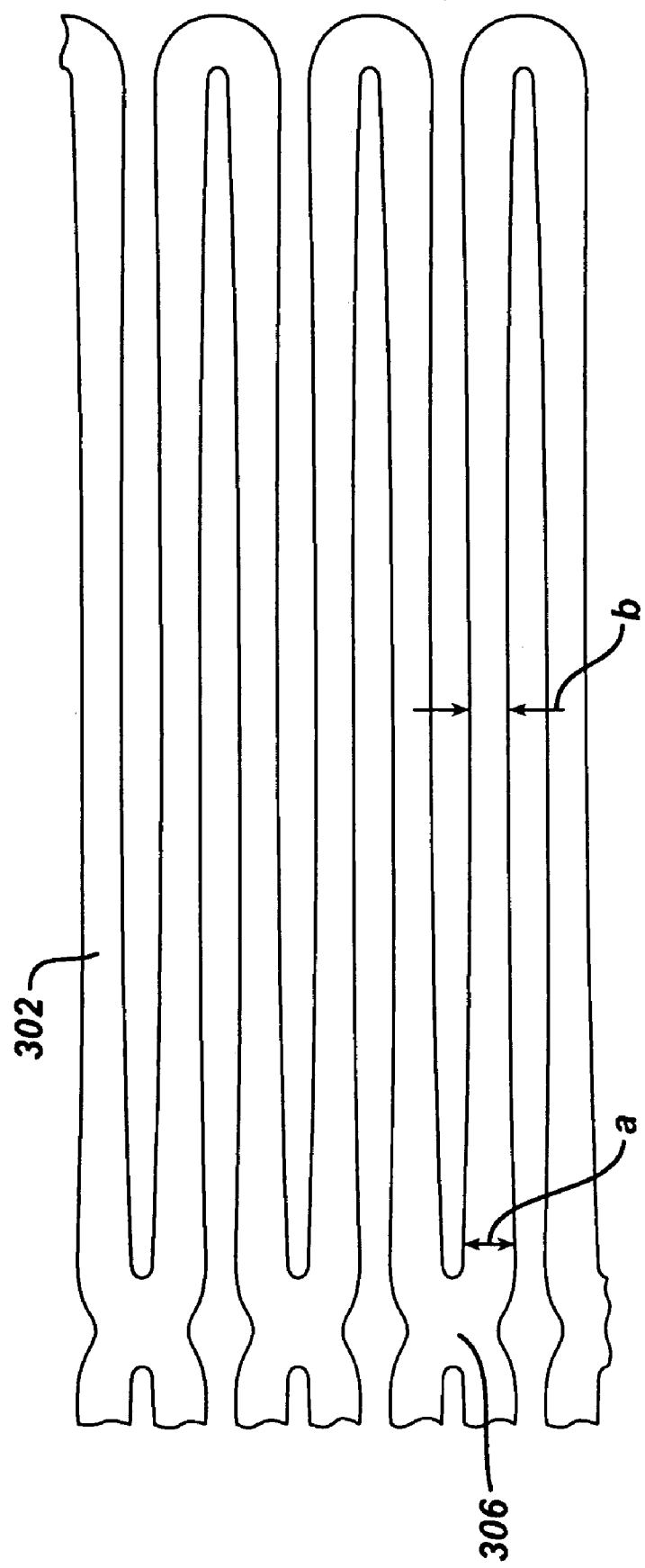

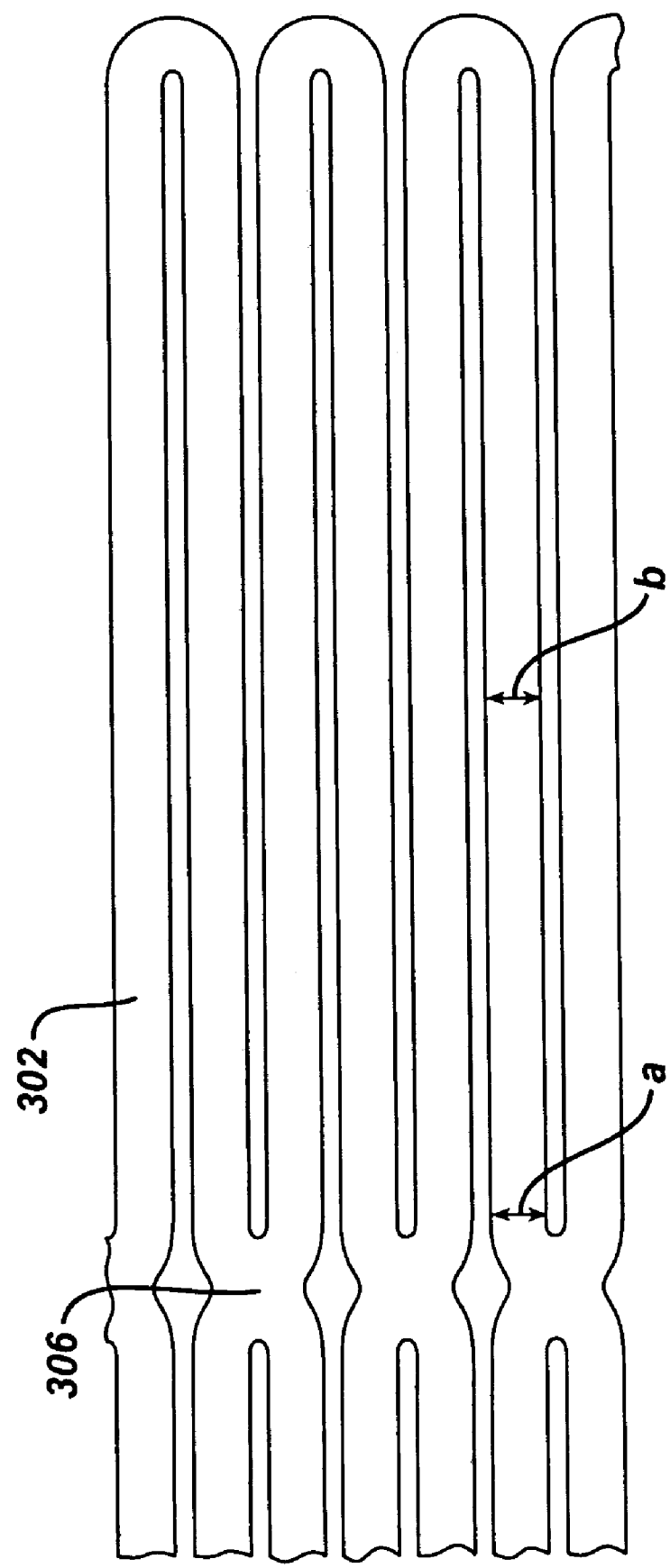

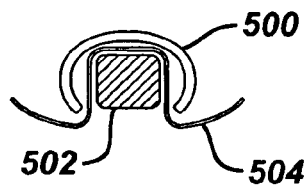
FIG. 5A
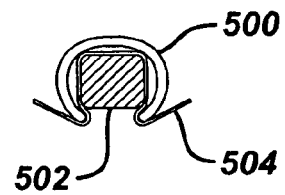
FIG. 5B
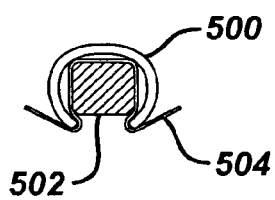
FIG. 5C
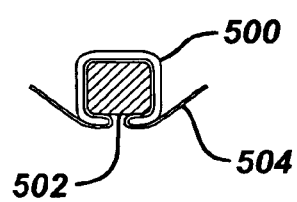
FIG. 5D
FIG. 6
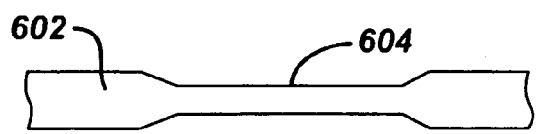
FIG. 7A
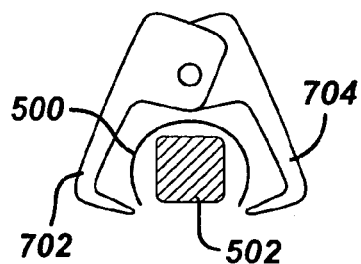
FIG. 7B
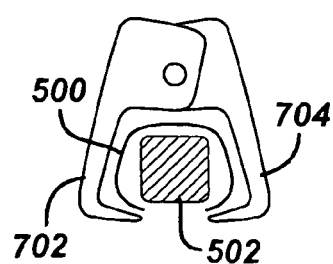
FIG. 7C
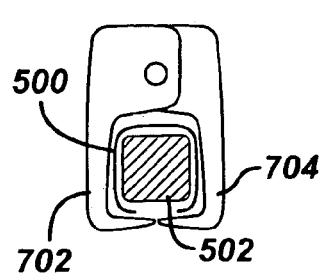

GRAFT MATERIAL ATTACHMENT DEVICE AND METHOD

BACKGROUND OF THE INVENTION

1. Field of the Invention

The present invention relates to devices and methods for repairing aneurysms and more particularly, to percutaneously and/or intraluminally delivered devices and methods for repairing aneurysms such as abdominal aortic aneurysms and thoracic aortic aneurysms. The present invention also relates to devices utilized to attach graft material to stents or other substrates for fabricating devices for repairing aneurysms and the like.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cutdown of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

SUMMARY OF THE INVENTION

The present invention overcomes the potential disadvantages associated with percutaneously delivered endoprostheses as briefly described above.

In accordance with one aspect, the present invention is directed to an attachment device. The attachment device comprises a deformable, partially tubular band having a slotted opening for accepting a portion of a first substantially flexible element and a portion of a second substrate element.

In accordance with another aspect, the present invention is directed to a stent graft. The stent graft comprises one or more stent structures, a biocompatible graft material affixed to the one or more stent structures, and at least one attachment device for securing the biocompatible graft material to the one or more stent structures. The at least one attachment device comprising a deformable, partially tubular band having a slotted opening for accepting a portion of the one or more stent structures and a portion of the biocompatible graft material.

In accordance with another aspect, the present invention is directed to a method for attaching graft material to a stent structure. The method comprises positioning graft material around a stent structure, positioning at least one attachment device such that the graft material is sandwiched between the at least one attachment device and a portion of the stent structure, and crimping the at least one attachment device around the graft material at the portion of the stent structure.

The abrasion resistant stent-graft of the present invention comprises at least one stent segment and a highly durable, abrasion-resistant graft material attached thereto. The graft material may be attached to the at least one stent segment in any number of ways. The stent-graft may be utilized as a component of a larger system, for example, in a system for repairing abdominal aortic aneurysms, or as a stand-alone device. In either embodiment, the stent-graft is utilized as a fluid carrying conduit that is preferably percutaneously delivered, but may also be utilized surgically. The at least one stent segment may comprise any suitable scaffold structure and may be fabricated from any number of biocompatible materials. The at least one stent segment may be self-expanding or balloon expandable.

The abrasion resistant stent-graft of the present invention is preferably percutaneously delivered, and as such it is preferably designed with the smallest diameter possible. In order to achieve the smallest diameter possible, thinner graft materials are needed. However, stent-grafts are typically positioned within the body in vessels that have relatively high hydrodynamic forces, thus requiring graft materials which are able to withstand these forces. Essentially, these forces tend to wear the graft material at the points where it is connected to the at least one stent segment. Over time, the graft material may develop microleaks which obviously defeat the purpose of the stent-graft, namely, as a by-pass conduit. Accordingly, the abrasion resistant stent-graft of the present invention utilizes a biocompatible, high tensile strength, abrasion resistant, highly durable yarn which may be woven, knitted or braided into a graft material without sacrificing diameter.

The yarn or thread may comprise a single component or it may be blended with one or more other suitable materials to achieve various desirable characteristics, including abrasion resistance, flexibility and thinness. One such yarn comprises ultra high molecular weight polyethylene, which is commercially available. Accordingly, the abrasion resistant stent-graft of the present invention is a highly durable stent-graft which, because of its thin graft material, may be percutaneously delivered more easily than present stent-grafts.

The attachment device of the present invention comprises a clip or band structure that may be utilized to attach graft material to a stent thereby forming a covered stent, stent-graft, endoleg, endoprosthesis or any other device that requires a covering to be attached to a substrate. The attachment device may be fitted over the graft material and a segment of the stent, such as a stent strut, and then deformed to create a snug fit around the stent segment with the graft material sandwiched therebetween. A device, similar to pliers, may be utilized to deform or crimp the attachment device to the stent segment.

The attachment device of the present invention may be utilized to secure or attach graft material to a stent or stent like structure without the need for sutures or staples as is currently utilized. Alternately, the attachment device of the present invention may be utilized in combination with other securing means such as staples or sutures.

The attachment device of the present invention offers a number of advantages over existing attachment technology. The attachment device does not make direct contact with the stent because the graft material is sandwiched therebetween. If the attachment device were constructed from a metallic material different from the metallic material comprising the stent, and if the two components were in direct contact, there may be corrosion due to galvanic action. The attachment device does not require a breach of the graft material. Accordingly, there is less likely of a chance of leakage and graft failure due to tearing. The attachment device is positioned on the surface of the stent-graft that is in contact with the vessel wall; therefore, in the unlikely even the attachment device becomes dislodged, it will be trapped between the vessel wall and the stent-graft and pose substantially no threat of creating a particle emboli. The attachment device may serve a dual role. If needed, the attachment device may be fabricated from a highly radiopaque material and function as a marker band for proper placement of the stent-graft.

The attachment device of the present invention is simple and inexpensive to manufacture. The attachment device is also simple to utilize.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 2C is an enlarged plan view of a section of the stent segment of FIG. 2.

FIG. 2D is an enlarged plan view of a section of the stent segment of FIG. 2.

FIGS. 5a-5d, are sectional views of the attachment device in accordance with the present invention.

FIG. 6 is a sectional view of a modified stent segment in accordance with the present invention.

FIGS. 7a-c are diagrammatic representations of a crimping device in accordance with the present invention.

DETAILED DESCRIPTION OF THE PREFERRED EMBODIMENTS

The present invention is directed to an endovascular graft which may be utilized as a component in a system for use in treating or repairing aneurysms. Systems for treating or repairing aneurysms such as abdominal aortic aneurysms and thoracic aortic aneurysms come in many forms. A typical system includes an anchoring and/or sealing component which is positioned in healthy tissue above the aneurysm and one or more grafts which are in fluid communication with the anchoring and/or sealing component and extend through the aneurysm and anchor in healthy tissue below the aneurysm. Essentially, the grafts are the components of the system that are utilized to establish a fluid flow path from one section of an artery to another section of the same or different artery, thereby bypassing the diseased portion of the artery. Current systems are preferably percutaneously delivered and deployed.

As stated above, the present invention is directed to one component of an aneurysm repair system; namely, the endovascular graft of stent-graft. Accordingly, the following detailed description is directed to the endovascular graft. The endovascular graft comprises at least one stent segment and a highly durable, abrasion-resistant graft material attached thereto. In other words, the endovascular graft of the present invention is supported internally by one or more individual stents, which are themselves connected to the graft in a manner which secures their position, for example, by sutures. It is important to note that while one particular stent design is discussed in detail below, the graft of the present invention may incorporate any number of suitable stent designs, including self-expanding stents and balloon expandable stents. In addition, the endovascular graft may comprise a device formed solely from the graft material.

Figure 1:
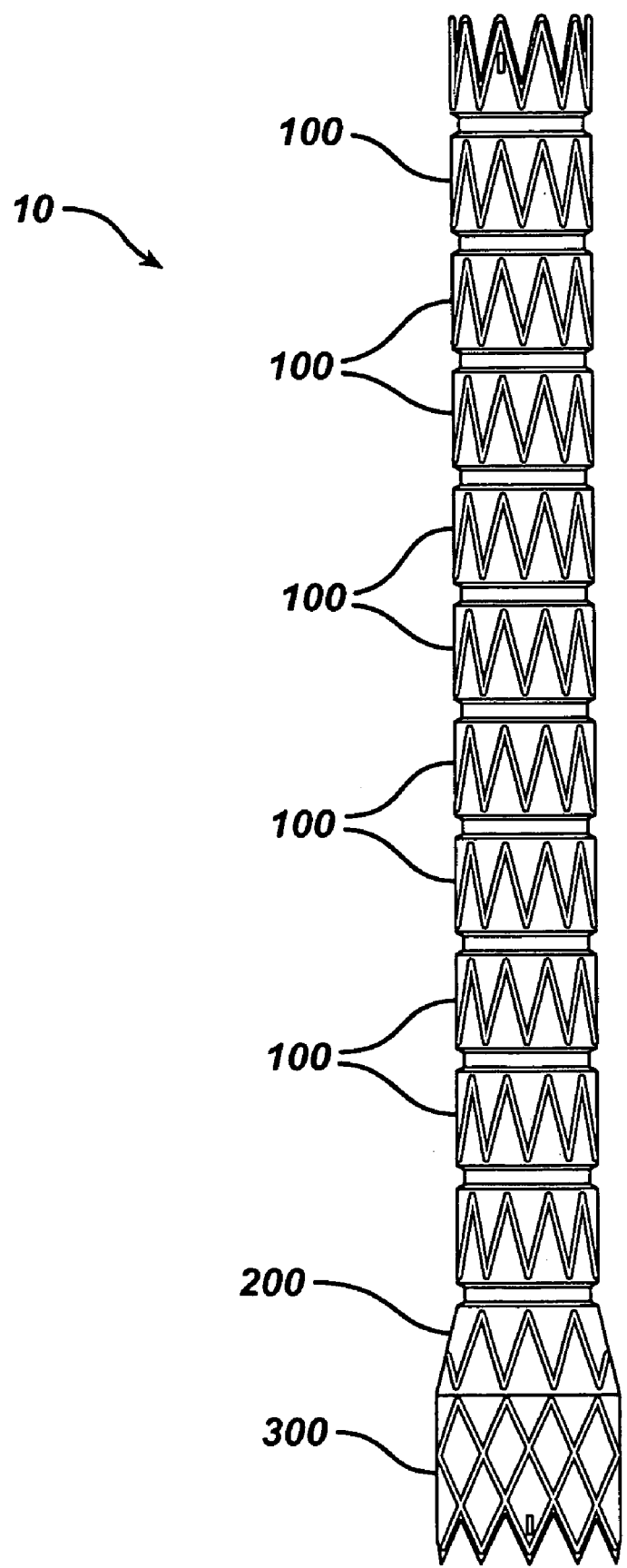
FIG. 1 is an elevational view of an endovascular graft in accordance with the present invention.

FIG. 1 illustrates an exemplary embodiment of an endovascular graft 10 in accordance with the present invention. The exemplary endovascular graft 10 comprises one or more first stent segments 100, one second stent segment 200 and a third stent segment 300. In order to illustrate the relationship of the various components comprising the endovascular graft 10, the endovascular graft is illustrated in the figure as though the graft material were transparent. In a typical use scenario, the third stent segment 300 would be anchored in healthy tissue below the aneurysm and the uppermost first stent segment 100 would be in fluid communication with an anchoring and/or sealing component as briefly described above. It is important to note, however, that depending on the design of the system, an anchoring and/or sealing component may not be necessary. The second stent segment 200 comprises a tapered profile, having a diameter at one end equal to that of the first stent segments 100 and a diameter at the other end equal to that of the third stent segment 300. The length of the endovascular graft may be varied by the number of first stent segments 100 utilized.

Figure 2:
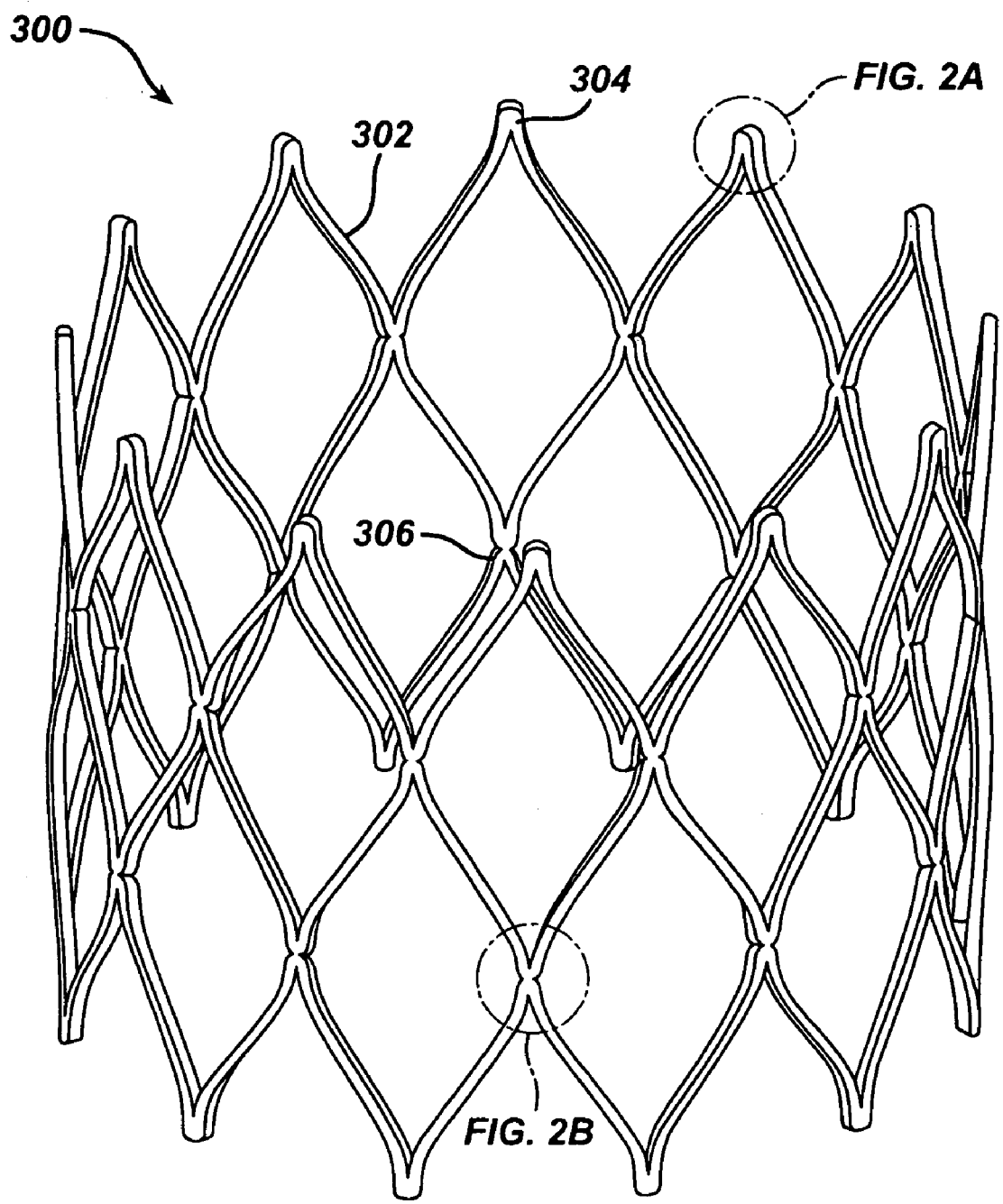
FIG. 2 is a perspective view of an expanded stent segment of the endovascula graft in accordance with the present invention.
Figure 2A:
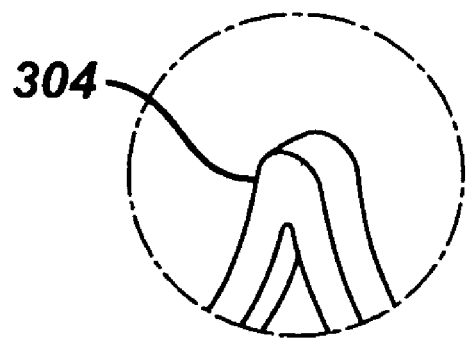
FIG. 2A is a fragmentary perspective view of a portion of the stent segment of FIG. 2.
Figure 2B:
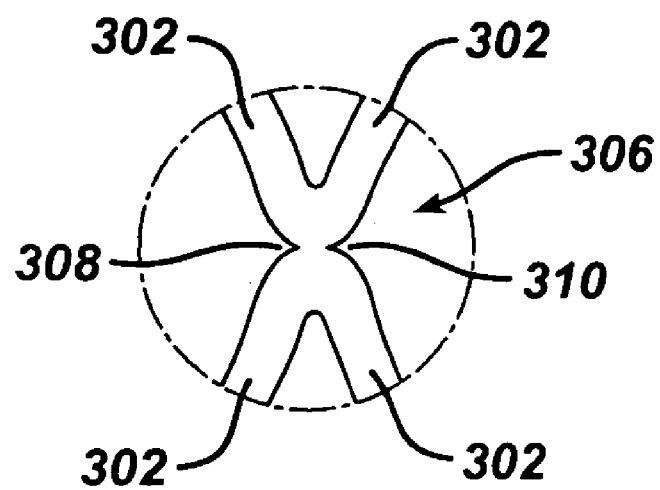
FIG. 2B is a fragmentary perspective view of a portion of the stent segment of FIG. 2.

FIG. 2 is a detailed perspective view of an exemplary embodiment of the third stent segment 300. The third stent segment 300 comprises a plurality of struts 302 connected in a substantially zigzag pattern. As illustrated, the exemplary third stent segment 300 comprises three sets of zigzag-connected stents 302, thereby forming substantially diamond-shaped cells. The non-connected apex 304 of each diamond shaped cell, illustrated in greater detail in FIG. 2A, comprises a smooth, uniform width curved region formed at the intersection of two stents 302 of each diamond-shaped cell. This shape is cut directly into the stent segment 300 during the initial machining steps, typically laser cutting, as is explained in detail subsequently, and is maintained during all subsequent finishing processing. The junctions 306 between the zigzag-connected stents 302, illustrated in greater detail in FIG. 2B occurs at the intersection of four struts 302. Preferably, each junction 306 of four struts 302 comprises two indentations 308 and 310 as illustrated in FIG. 2B.

The regions proximate the non-connected apexes 304 and the junctions 306 are generally the highest stress regions in the third stent segment 300. To minimize the stresses in these regions, these regions are designed to maintain uniform beam widths proximate where the struts 302 interconnect. Beam width refers to the width of a strut 306. Indentations 308 and 310 are cut or machined into the junctions 306 to maintain a uniform beam width in this area, which is generally subject to the highest stress. Essentially, by designing the junctions 306 to maintain uniform beam widths, the stress and strain that would normally build up in a concentrated area, proximate the junction 306, is allowed to spread out into the connecting regions, thereby lowering the peak values of the stress and strain in the stent structure.

To further minimize the maximum stresses in the struts 302 of the third stent segment 300, the struts 302 may have a tapering width. For example, in one exemplary embodiment, the struts 302 may be designed to become wider as it approaches a junction 306. FIG. 2C is an enlarged partial view of the third sent segment 300 in its expanded conditions which illustrates the tapering width of the struts 302. In this exemplary embodiment, the strut 302 proximate the junction 306 (width a) is about 0.025 cm and gradually tapers to a dimension of about 0.0178 cm in the mid-region of the strut 302 (width b). By tapering the struts' widths, the stresses in the struts 302 adjacent the junction 306 is spread out away from the junction 306. The tapering of the struts 302 is accomplished during the machining of the tube of material from which the stent 300 is cut, as described in detail subsequently. However, by tapering the struts 302 in this manner, there is a tradeoff. The stent segment 300 becomes somewhat less resistant to localized deformations, caused for example, by a protrusion within the vessel lumen. This localized deformation may lead to a local torsional loading on some of the struts 302, and, therefore, since the struts 302 in this exemplary embodiment have a relatively significant portion of their length with a reduced width, their torsional rigidity is reduced.

If maximizing the resistance to localized deformation is preferred, the struts 302 may be maintained at a uniform width, or more preferably have a reverse taper, as illustrated in FIG. 2D, wherein the width at point a is less than the width at point b. In this exemplary embodiment, the reverse taper struts 302 are about 0.025 cm proximate the junction 306 and about 0.028 cm in the central region of the struts. While this reverse taper tends to increase the stresses somewhat proximate the junctions 306, this increase is very small relative to the decrease in stresses gained by having the side indentations 308, 310 illustrated in FIG. 2B, as well as the uniform width connections illustrated in FIG. 2A. In addition, since the reverse taper serves to increase the torsional rigidity of the strut 302, the stent structure resists local deformation and tends to maintain a substantially circular cross-sectional geometry, even if the lumen into which the stent is positioned in non-circular in cross-section.

In a preferred exemplary embodiment, the third stent segment 300 is fabricated from a laser cut tube, as described in detail subsequently, of initial dimensions 0.229 cm inside diameter by 0.318 cm outside diameter. The struts 302 are preferably 0.0229 cm wide adjacent the four strut junctions 306 and six mm long, with a reverse taper strut width. Also, to minimize the number of different diameter combination of grafts systems, it is preferred that the third stent segment 300 have an expanded diameter of sixteen mm. Similarly, the proximal portion of the graft material forming the legs is flared, having a diameter of sixteen mm. This single diameter for the third stent segment of the graft system would enable its use in arteries having a non-aneurysmal region of a diameter from between eight and fourteen mm in diameter. It is also contemplated that multiple diameter combinations of third stent segment 300 and graft flare would be desirable.

Figure 3:
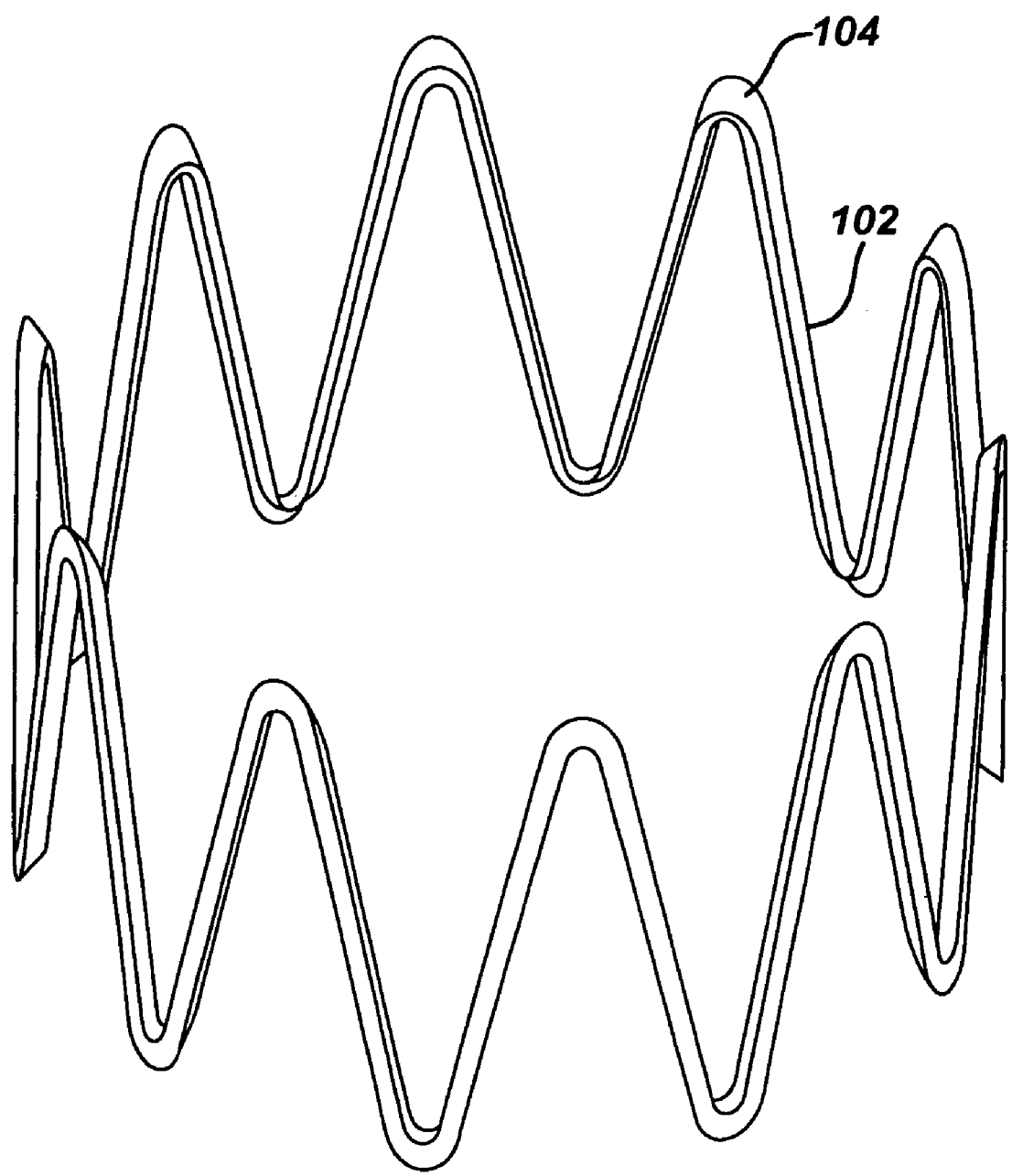
FIG. 3 is a perspective view of another expanded stent segment of the endovascular graft in accordance with the present invention.

Referring back to FIG. 1, the one or more first stent segments 100 are also formed from a shape set laser cut tube, similar to the third stent segment 300 described above. The one or more first stent segments 100 comprise a single circumferential row of zigzag or sinusoidally arranged elements. In the exemplary embodiment illustrated in FIG. 1, and in greater detail in FIG. 3, the first stent segment 100 comprises ten zigzag or sinusoidal undulations. The one or more first stent segments 100 are formed with uniform width connections at the intersections 104 of the struts 102 forming the zigzag or sinusoidal pattern. The one or more first stent segments 100 are preferably cut from tubing having an inside diameter of 0.251 cm and an outside diameter of 0.317 cm. The strut widths are preferably about 0.33 cm wide adjacent strut intersections 104 and the struts 102 are preferably seven mm long and the one or more first stent segments 100 are preferably eleven mm in diameter when expanded.

Referring back to FIG. 1, the second stent segment 200 comprises a tapered profile, having a diameter at one end which is the same as the one or more first stent segments 100, and a diameter at the other end matching the diameter of the third stent segment 300. The second stent segment 200 is identical to the one or more first stent segments 100 except for the taper.

As is explained in detail subsequently, the stent segments 100, 200 and 300 are secured in position by the graft material.

The first, second and third stent segments 100, 200, 300 are preferably self-expandable and formed from a shape memory alloy. Such an alloy may be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising about 55.8 percent Ni by weight, commercially available under the trade designation NITINOL. This NiTi alloy undergoes a phase transformation at physiological temperatures. A stent made of this material is deformable when chilled. Thus, at low temperatures, for example, below twenty degrees centigrade, the stent is compressed so that it can be delivered to the desired location. The stent may be kept at low temperatures by circulating chilled saline solutions. The stent expands when the chilled saline is removed and it is exposed to higher temperatures within the patient's body, generally around thirty-seven degrees centigrade.

In preferred embodiments, each stent is fabricated from a single piece of alloy tubing. The tubing is laser cut, shape-set by placing the tubing on a mandrel, and heat-set to its desired expanded shape and size.

In preferred embodiments, the shape setting is performed in stages at five hundred degrees centigrade. That is, the stents are placed on sequentially larger mandrels and briefly heated to five hundred degrees centigrade. To minimize grain growth, the total time of exposure to a temperature of five hundred degrees centigrade is limited to five minutes. The stents are given their final shape set for four minutes at five hundred fifty degrees centigrade, and then aged to a temperature of four hundred seventy degrees centigrade to import the proper martensite to austenite transformation temperature, then blasted, as described in detail subsequently, before electropolishing. This heat treatment process provides for a stent that has a martensite to austenite transformation which occurs over a relatively narrow temperature range; for example, around fifteen degrees centigrade.

To improve the mechanical integrity of the stent, the rough edges left by the laser cutting are removed by combination of mechanical grit blasting and electropolishing. The grit blasting is performed to remove the brittle recast layer left by the laser cutting process. This layer is not readily removable by the electropolishing process, and if left intact, could lead to a brittle fracture of the stent struts. A solution of seventy percent methanol and thirty percent nitric acid at a temperature of minus forty degrees centgrade or less has been shown to work effectively as an electropolishing solution. Electrical parameters of the electropolishing are selected to remove approximately 0.00127 cm of material from the surfaces of the struts. The clean, electropolished surface is the final desired surface for attachment to the graft materials. This surface has been found to import good corrosion resistance, fatigue resistance, and wear resistance.

The graft material or component 400, as illustrated in FIG. 1, may be made from any number of suitable biocompatible materials, including woven, knitted, sutured, extruded, or cast materials comprising polyester, polytetrafluoroethylene, silicones, urethanes, and ultralight weight polyethylene, such as that commercially available under the trade designation SPECTRA™. The materials may be porous or nonporous. Exemplary materials include a woven polyester fabric made from DACRON™ or other suitable PET-type polymers.

In one exemplary embodiment, the fabric for the graft material is a forty denier (denier is defined in grams of nine thousand meters of a filament or yarn), twenty-seven filament polyester yarn, having about seventy to one-hundred end yarns per cm per face and thirty-two to forty-six pick yarns per cm face. At this weave density, the graft material is relatively impermeable to blood flow through the wall, but is relatively thin, ranging between 0.08 and 0.12 mm in wall thickness.

The graft component 400 is a single lumen tube and preferably has a taper and flared portion woven directly from the loom, as illustrated for the endovascular graft 10 shown in FIG. 1.

Prior to attachment of the graft component 400 to the stents 100, 200, 300, crimps are formed between the stent positions by placing the graft material on a shaped mandrel and thermally forming indentations in the surface. In the exemplary embodiment illustrated in FIGS. 1 and 4, the crimps 402 in the graft 400 are about two mm long and 0.5 mm deep. With these dimensions, the endovascular graft 10 can bend and flex while maintaining an open lumen. Also, prior to attachment of the graft component 400 to the stents 100, 200 300, the graft material is cut in a shape to mate with the end of each end stent.

As stated above, each of the stent segments 100, 200 and 300 is attached to the graft material 400. The graft material 400 may be attached to the stent segments 100, 200, 300 in any number of suitable ways. In one exemplary embodiment, the graft material 400 may be attached to the stent segments 100, 200, 300 by sutures.

The method of suturing stents in place is important for minimizing the relative motion or rubbing between the stent struts and the graft material. Because of the pulsatile motion of the vasculature and therefore the graft system, it is possible for relative motion to occur, particularly in areas where the graft system is in a bend, or if there are residual folds in the graft material, due to being constrained by the aorta or iliac arteries.

Figure 4:
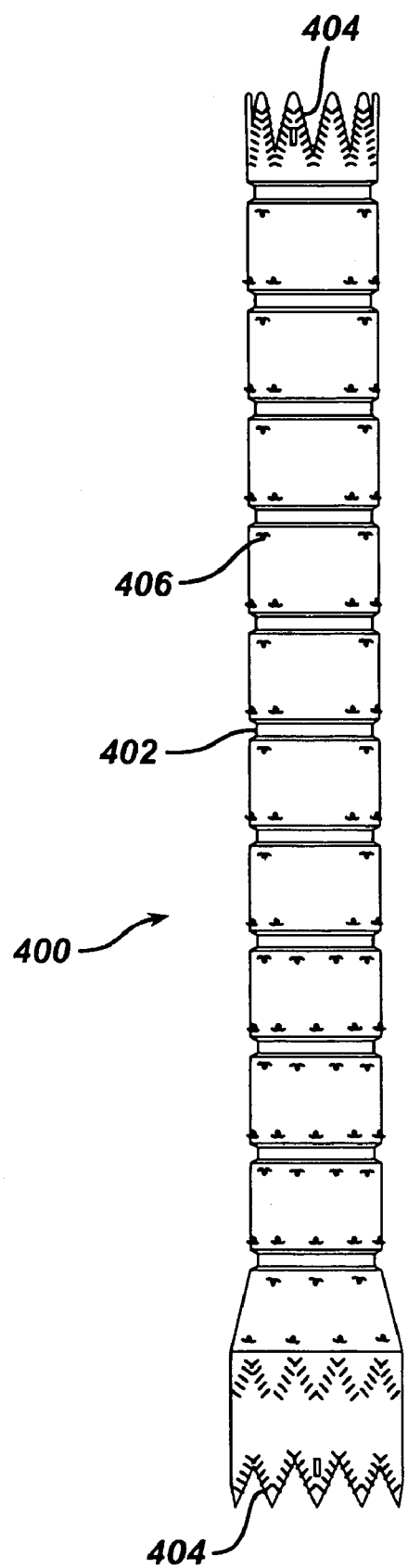
FIG. 4 is an elevational view of an endovascular graft in accordance with the present invention.

Ideally, each strut of each stent segment is secured to the graft material by sutures. In an exemplary embodiment, the suture material is blanket stitched to the stent segments at numerous points to securely fasten the graft material to the stent segments. As stated above, a secure hold is desirable in preventing relative motion in an environment in which the graft system experiences dynamic motion arising from pulsatile blood pressure, in addition to pulsation of the arteries that are in direct mechanical contact with the graft system. The stents nearest the aortic and iliac ends of the graft system (the uppermost first stent segment 100 and the third stent segment 300 respectively) are subject to the pulsatile motion arising from direct internal contact. These struts in particular should be well secured to the graft material. As illustrated in FIG. 4, the stitches 404 on the upper most first stent segment 100 are positioned along the entire zigzag arrangement of struts. The upper and lower apexes of the third stent segment may be stitched utilizing a similar configuration. It is difficult to manipulate the suture thread precisely around the struts that are located some distance away from an open end, accordingly, various other simpler stitches may be utilized on these struts, or no stitches may be utilized in these areas.

As illustrated in FIG. 4, each of the struts in the first stent segment 100 is secured to the graft material 400 which has been cut to match the shape of the stent segment 100. The blanket stitching 404 completely encircles the strut and bites into the graft material 400. Preferably, the stitch 404 encircles the strut at approximately five equally spaced locations. Each of the struts on each end of the third stent segment 300 is attached to the graft material, which has been cut to make the shape of the stent segment 300, in the same manner as the first stent segment 100.

A significant portion of the graft will not rest directly against vascular tissue. This portion of the graft will be within the dilated aneurysm itself. Therefore, this portion of the graft will not experience any significant pulsatile motion. For this reason, it is not necessary to secure the stent segments to the graft material as aggressively as the stent structure described above. Therefore, only point stitches 406 are necessary for securing these stents.

It is important to note that a wide variety of sutures are available. It is equally important to note that there are a number of alternative means for attaching the graft material to the stent, including welding, gluing and chemical bonding.

As stated above, In percutaneous procedures, size is a critical factor. One of the more significant determinants of the final diameter of the catheter system is the bulkiness of the graft material comprising the stent-graft. Accordingly, it is generally accepted that the highest impact on delivery catheter diameter may be achieved by fabricating stent-grafts having thinner walls.

Typical stent-grafts are fabricated from a woven polyester and are approximately 0.005 inches thick. For example, a stent-graft fabricated from a woven polyester low twist, forty denier, twenty-seven filament yarn having two-hundred thirty yarn ends per inch and one hundred yarn picks per inch, results in a graft material having a wall thickness of approximately 0.005 inches. The graft material is then attached to the inside or outside of a stent or multiple stent segments as described above. Appreciable gains may be achieved in having a graft material thickness in the range from about 0.002 inches to about 0.003 inches.

For a woven graft, as described above, the wall thickness is determined primarily by weave density and yarn thickness or bulkiness. It is desirable to have a graft which is packed tight enough to prevent significant blood seepage, but not so tight that the yarn bundles pile up on each other. The weaving parameters described above result in just such a graft for the particular yarn described. At this density, the graft material is about as thin walled as it can be without significant permeability. Also, the yarn described above is only lightly twisted, so as the yarn bundles cross over one another, they tend to flatten out. Higher twisting would both make the graft more permeable and thicker, and the yarn bundle would tend to remain cylindrical at the crossover points. The only remaining parameter that can be utilized to thin the graft is smaller yarn bundles.

There are two variables which influence yarn bundle size; namely, the number of filaments per bundle, and the size or weight of each individual filament. The forty denier, twenty-seven filament polyester yarn described above has a relatively small filament size and a relatively low number of filaments. However, in theory, a much smaller yarn bundle could be contemplated with either few filaments, smaller filaments, or both. For example, a twenty denier yarn bundle could be made from fourteen filaments of the same diameter as described above. If this yarn were woven into a graft material with an appropriately dense weave, one would expect a graft material having a thickness of approximately 0.0025 inches. While this may work as an acceptable graft, it is possible that the long-term integrity of such a graft may not be acceptable due to the forces described above.

The graft material may be formed utilizing any number of techniques, including weaving, knitting and braiding. Weaving involves the interlacing, at right angles, of two systems of threads known as warp and filling. Warp threads run lengthwise in a woven fabric and filling threads run cross-wise. Knitting is the process of making fabric by interlocking a series of loops of one or more threads. Braiding involves crossing diagonally and lengthwise several threads of any of the major textile fibers to obtain a certain width effect, pattern or style.

A growing concern with a number of endovascular graft systems has been that over time, holes may develop in the stent-graft wall, which can lead to blood leakage and possible aneurysm rupture. There is only a limited understanding of the mechanism of hole formation; however, it is generally believed to be related to what has been termed chronic micromotion between the metallic stent support structures and the graft material. Eventually, this micro-motion may cause the graft material to wear away, thereby creating holes.

One potential way in which to overcome this problem is by more tightly binding the graft material to the stent in areas exhibiting the highest possibility of micro-motion. There are numerous ways by which the graft material may be attached to the stent, for example, polymeric sutures. Accordingly, it may be possible to simply create a thinner polyester graft material as described above, more tightly secure it to the stent in areas which exhibit the greatest potential for micro-motion, and have a lower profile, longer wear resistant stent-graft. However, it would also be beneficial to consider alternate materials for fabricating a significantly thinner graft material with high wear resistance. Higher strength and/or tougher materials may yield a much thinner stent-graft conduit without sacrificing long-term integrity. In fact, some of the materials that may be utilized are so much stronger and tougher than Dacron® polyester, that a significantly thinner stent-graft constructed of these materials may be substantially stronger and more wear resistant than currently available stent-grafts.

There are a number of new, higher performance fibers that are significantly stronger and tougher than polyester, and which are also biocompatible. Whereas, Dacron® polyester has a tenacity of approximately nine grams per denier, many high performance fibers have tenacities in the range from about thirty-five to about forty-five grams per denier. The more preferred fibers from a strength standpoint for consideration for use in an ultra thin walled stent-graft material, approximately, 0.002 to 0.003 inches include polyaramid, polyphynelenebenzobisoxazole, liquid crystal polymer and ultra high molecular weight polyethylene. From a purely strength standpoint, all of these materials are suitable for ultra-thin walled stent-graft applications. However, from a biostability standpoint, ultra high molecular weight polyethylene fibers may offer a slight advantage in the fact that their basic chemistry is polyethylene, which is known to be relatively inert in biological applications.

Another important consideration for the above-described fibers is their availability in fine denier yarns. With current stent-grafts fabricated from a forty denier polymer yarn, it would be difficult to fabricate a stent-graft having thinner walls unless the yarn is of a finer denier. A liquid crystal polymer sold under the tradename Vectran is available as a twenty-five denier yarn. A ultra high molecular weight polyethylene sold under the tradename Spectra is available as a thirty-denier yarn. Another ultra high molecular weight polyethylene sold under the tradename Dyneema is available as a twenty to twenty-five denier yarn. It is also important to consider that ultra high molecular weight polyethylene fibers only have a density of 0.97 versus 1.38, so that the same denier yarn would be bulkier in ultra high molecular weight polyethylene, however, due to the substantial improvement in tensile and abrasive properties, much less ultra high molecular weight polyethylene would be necessary to obtain equivalent material properties.

Polyethylene is a long chain organic polymer formed by the polymerization of ethylene. When formed under low pressure, it will form long polymer chains which increases its resistance to fracture. Ultra high molecular weight polyethylene typically has between six and twelve million ethylene units per molecule. Ultra high molecular weight polyethylene has a low coefficient of friction, a high molecular weight and a high density. Accordingly, a fabric made from ultra high molecular weight polyethylene is highly abrasion resistant, highly impact resistant, and highly resistant to damage by water, salt or fresh. Ultra high molecular weight polyethylene monofilaments have a high tensile strength with the associated advantage of stretch resistance and elasticity. These properties make it especially suitable for tortuous body passageways.

As stated above, polyethylene has a long documented history of biocompatability. Given this level of biocompatability, coupled with its physical attributes, ultra high molecular weight polyethylene is the preferred yarn for use as a graft material. The ultra high molecular weight polyethylene yarn may be woven, knitted or braided to form the graft material and attached to the one or more stent segments as described above. The graft material may also be used as a strand alone device for surgical applications or combined with the one or more stents for endovascular delivery.

In alternate exemplary embodiments, the ultra high molecular weight polyethylene yarn may be blended with a dissimilar material, for example, Dacron® polyester, to manufacture a graft material with altered bulk properties; e.g., stretch potential, while retaining strength and abrasion resistance. In yet other alternate exemplary embodiment, the monofilament of ultra high molecular weight polyethylene may be blended together with another material to attain a true blended yarn such that a fiber or monofilament of one material can be placed next to a monofilament of a second material (third, fourth . . . ) to create a resultant yarn which possesses properties that differ from each of its monofilaments.

As described above, graft material may be attached to stents or stent segments in any number of suitable ways. In one exemplary embodiment, the graft material may be attached by suturing the graft material to the stent lattice at predetermined locations as described herein. In an alternate exemplary embodiment, the graft material may be attached to the stent or stent segments via an attachment device that holds or sandwiches the graft material between itself and a portion of the stent. In this approach, the graft material is not punctured. The attachment device may comprise any suitable configuration such as a band or clip and may be formed from any suitable material. It is important to note that the attachment device may be utilized for applications other than the attachment of graft material to stents or stent segments. For example, the attachment device may be utilized to attach or secure any substantially flexible material or covering to another element or substrate.

Referring to FIGS. 5a-5d, there is illustrated an exemplary attachment device 500 in accordance with the present invention. FIGS. 5a-5d illustrate a progression of cross-sectional views of the attachment device 500, a segment of a stent 502, and a segment of graft material 504 as the attachment device 500 is positioned and secured into place. As illustrated in FIG. 5a, the attachment device 500 is positioned over the graft material 504 and a segment of a stent 502. The attachment device 500 may comprise any suitable shape, size and material. Preferably, the attachment device 500 comprises a shape and material that allows it to be positioned over the graft material 504 and stent segment 502 and then crimped or otherwise manipulated into a configuration such that it substantially conforms to the shape of the stent segment 502 as illustrated in FIG. 5d. With this snug fit, the overall profile of the stent-graft or other device will not be significantly impacted or affected. In addition, the attachment device 500 preferably comprises a material that exhibits minimal fatigue wear when undergoing the crimping process.

In the exemplary embodiment, the attachment device 500 comprises a simple band, clip or ring structure formed by creating a longitudinal slit or opening in a tubular structure. The slit or opening may be formed by any suitable machining technique. The attachment device 500, as stated above, may be formed from any suitable material, including plastics and metals. For example, the attachment device may comprise polymeric materials or various metallic materials such as stainless steel or tantalum. Depending on the material utilized for the stent, it may be desirable to utilize a highly radiopaque material for the attachment device 500 so that it may serve the dual purpose of securing the graft material to the stent and act as a marker band for properly deploying the stent-graft in position. Metallic materials such as tantalum are highly radiopaque. If the stent is formed from a highly radiopaque material or utilizes other marker elements, then any other suitable material may be utilized for the attachment device 500.

In alternate exemplary embodiments, the attachment device 500 may be formed by mechanical shape setting of a thermal or shape memory material or by ultrasonic welding.

Once the attachment device 500 is positioned around the stent segment 502 with the graft material 504 sandwiched therebetween, it may be crimped snuggly around the stent segment 502 as illustrated in the progression of FIGS. 5a through 5d. As illustrated in FIG. 5d, the attachment device 500 securely holds the graft material 504 to the stent segment 502 without creating any openings in the graft material 504. The attachment device 500 may be utilized anywhere the sutures described above may be utilized. In addition, if the attachment devices 500 are utilized as markers, the shape and/or size of the attachment devices 500 may vary depending on their location on the stent or stent segment so that exact positioning may be achieved.

As described above, by conforming the attachment device 500 to the stent 502, the graft material 504 may be securely held in position and the overall profile of the stent-graft will not be significantly impacted. In order to further minimize the impact on the profile of the stent-graft, the thickness of the attachment device 500 may be maintained to less than that of the suture/suture knot.

In an alternate exemplary embodiment, the attachment device 500 and/or the stent segment 502 may be modified such that the attachment device 500 slips or gives as the stent moves. For example, some or all of the attachment devices 500 may be fixed in position by complete crimping or some or all of the attachment devices 500 may be slidably mounted to accommodate stent lengthening during crimping. The attachment devices 500 may be slidably mounted by less than complete crimping, by designing the attachment devices 500 to allow movement even when fully crimped or by modifying some or all of the stent segments. For example, referring to FIG. 6, there is illustrated a stent segment 602 having a reduced profile section 604 that would allow the attachment device 500 to move in that area, but not beyond the area.

As described above, in one exemplary embodiment, the attachment device 500 comprises a simple band, clip or ring structure formed from a tube with a longitudinal slit. The slit is expanded to fit over the stent element, for example, the stent struts, and graft material, and then crimped, squeezed or deformed to wrap around the strut and graft material. The attachment device 500 may also be made of a tubular structure that is bent or deformed into a substantially kidney shape, then placed and crimped. This design would preferably minimize and damage caused by any potential sharp edges formed during crimping. Similar shapes such as a disc could be used and formed to wrap around the stent segment and graft material.

The attachment device 500, as illustrated in FIGS. 5a-5d may be utilized for attaching an implantable graft material to a stent such as used in the fabrication of a covered stent, stent-graft, endoleg or any other device that requires a covering to be attached to a substrate. As described above, in one exemplary embodiment, the attachment device 500 comprises a hypotube segment that has a slit or slice cut longitudinally such that as to create an opening for accepting the stent and graft fabric. The attachment device 500 is fitted onto the stent strut 502 and graft material 504 by slipping the stent 502 and graft material 504 through the slit as illustrated in FIG. 5a. Then the attachment device 500 is crimped to capture or hold the stent 502 and graft material 504 together as illustrated in FIG. 5d.

FIGS. 7a-c illustrate an exemplary crimping tool 700 that may be utilized to squeeze or crimp the attachment device 500 and deform it into its final shape. As illustrated, the crimping tool 700 comprises a pair of pivotally moveable jaws 702,704. In operation, the jaws 702,704 are opened a distance sufficient to fit around the attachment device 500, the stent strut 502 and the graft material 504 as illustrated in FIG. 7a. Once positioned properly, the jaws 702,704 are pivoted together, as illustrated in FIG. 7b, until the attachment device 500 fits snuggly around the stent strut 502 and graft material 504, as illustrated in FIG. 7c.

The jaws 702,704 of the crimping tool 700 may comprise any suitable configuration and may be formed from any suitable material. The crimping tool 700 is preferably configured like pliers with jaws 702,704 being configured to the shape of stent struts. Accordingly, different crimping tools 700 may be employed with stents having different struts shapes. Preferably, the crimping tool 700 may be configured such that the jaws 702,704 are interchangeable or that they may be fitted with inserts that conform to the shape of the particular strut. In addition, the crimping tool 700 may comprise a means for limiting the pressure applied to the struts and graft material. For example, the crimping tool 700 may comprise a mechanical stop that limits the composition of the jaws 702,704 or an adjustable stop similar to mechanism utilized in vise grips.

It is important to note that the attachment device of the present invention may be utilized to attach graft material or graft like material to any number of medical devices. The above-described stents and graft material (FIGS. 1-4) are for illustrative purposes and not intended to limit the scope of the claimed invention. In other words, the attachment device of the present invention may be utilized with any stent and with any graft material, or as stated above, the attachment device may be utilized to attach or secure any substantially flexible material or covering to another element or substrate.

The attachment device of the present invention offers a number of substantial advantages over existing attachment technology. The attachment device would be insulated from the stent framework by a layer of graft material which in turn reduces or substantially eliminates bimetallic coupling thus reducing or substantially eliminating the risk of galvanic corrosion. The attachment device does not require a breach of the graft material to secure the graft to the stent. This eliminates the suture or staple holes that are created with attachments of other designs and greatly reduces the chance of leaking through at the attachment sites. No portion of the attachment device needs to be placed interior of the graft material and therefore if an attachment device failed in a long term situation it would be captured or trapped between the outside of the stent graft and the vessel wall minimizing the chance of particle emboli. The manufacture of a stent graft utilizing the attachment device of the present invention is greatly simplified since all assembly work may be done from the exterior of the stent. The attachment device of the present invention is a low profile device and may serve a dual role as a connection means and radiopaque marker.

It is important to note that the attachment device 500 of the present invention may be utilized alone or in combination with other attachment means including sutures and/or staples as described above.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. A stent graft comprising:
   one or more stent segments, each stent segment comprising a plurality of struts connected in a substantially zigzag pattern, wherein one or more struts in each stent segment comprises a reduced profile section, each of the stent segments having a gap therebetween;
   a biocompatible graft material affixed to the one or more stent segments, the graft material having indented sections in the regions of the gaps between the stent segments; and
   at least one attachment device for securing the biocompatible graft material to the one or more stent segments, the at least one attachment device comprising a deformable, partially tubular band having a slotted opening for accepting a portion of a strut and a portion of the biocompatible graft material, the deformable, partially tubular band having a substantially linear initial shape and being deformable to substantially surround and conform to the shape of the strut at the reduced profile section with a substantially rectangular final shape, thereby slidably engaging the graft material to the strut and graft material without puncturing either the graft material or the strut, the deformable, partially tubular band being configured to allow relative movement between the biocompatible graft material and the strut and configured to slidably secure the biocompatible graft material to the strut of the one or more stent segments, the at least one attachment device comprises a metallic material.

2. The stent graft according to claim 1, wherein the graft material comprises ultra high molecular weight polyethylene.

3. The stent graft according to claim 2, wherein the ultra high molecular weight polyethylene graft material comprises a yarn having a weight in the range from about twenty denier to about thirty denier.

4. The stent graft according to claim 1, wherein the graft material comprises polyaramid.

5. The stent graft according to claim 1, wherein the graft material comprises polyphynelenebenzobisoxazole.

6. The stent graft according to claim 1, wherein the graft material comprises liquid crystal polymer.

7. The stent graft according to claim 1, wherein the graft material comprises blends of ultra high molecular weight polyethylene.

8. The stent graft according to claim 1, wherein the graft material is woven.

9. The stent graft according to claim 1, wherein the graft material is knitted.

10. The stent graft according to claim 1, wherein the graft material is braided.

11. The stent graft according to claim 1, wherein the at least one attachment device comprises a polymeric material.

* * * * *